(12) United States Patent
Williams et al.

(10) Patent No.: US 11,779,343 B2
(45) Date of Patent: *Oct. 10, 2023

(54) STAPLE RELOAD ASSEMBLY WITH RELEASABLE KNIFE

(71) Applicant: Covidien LP, Mansfield, MA (US)

(72) Inventors: Justin Williams, Southbury, CT (US);
Russell Pribanic, Roxbury, CT (US);
David A. Nicholas, Trumbull, CT (US)

(73) Assignee: Covidien LP

( * ) Notice: Subject to any disclaimer, the term of this patent is extended or adjusted under 35 U.S.C. 154(b) by 149 days.

This patent is subject to a terminal disclaimer.

(21) Appl. No.: 17/148,842

(22) Filed: Jan. 14, 2021

(65) Prior Publication Data
US 2021/0259694 A1 Aug. 26, 2021

Related U.S. Application Data

(60) Provisional application No. 62/981,636, filed on Feb. 26, 2020.

(51) Int. Cl.
*A61B 17/00* (2006.01)
*A61B 17/115* (2006.01)

(52) U.S. Cl.
CPC . *A61B 17/1155* (2013.01); *A61B 2017/00477* (2013.01)

(58) Field of Classification Search
CPC .... A61B 17/07207; A61B 2017/00039; A61B 2017/00486; A61B 2017/00876; A61B 2017/07257; A61B 2017/07271; A61B 2017/07285; A61B 2562/0223; A61B 2017/00017; A61B 2017/00398; A61B 2017/0046; A61B 2017/2927; A61B 2560/0223; A61B 17/1155; A61B 2017/00477; A61B 2017/00473;
(Continued)

(56) References Cited

U.S. PATENT DOCUMENTS 3,108,828 A 10/1963 Kus
3,193,165 A 7/1965 Akhalaya et al.
3,388,847 A 6/1968 Kasulin et al.
(Continued)

FOREIGN PATENT DOCUMENTS

CA 908529 A 8/1972
CA 2530141 C * 7/2007 ........... A61B 17/115
(Continued)

OTHER PUBLICATIONS

European Search Report dated Apr. 30, 2021, issued in corresponding EP Appln. No. 21159214, 8 pages.

*Primary Examiner* — Robert F Long
(74) *Attorney, Agent, or Firm* — Carter, DeLuca & Farrell LLP

(57) ABSTRACT

A surgical stapling device includes an anvil assembly and a reload assembly that includes a knife and a knife carrier. The knife is releasably coupled to the knife carrier and is embedded in a cut ring of the anvil assembly when the stapling device is fired. The knife is separable from the knife carrier upon application of a predetermined force on the knife. The predetermined force is applied to the knife after the stapling device is fired by moving the anvil assembly in relation to the reload assembly from a clamped position to an open position.

3 Claims, 9 Drawing Sheets

(58) Field of Classification Search
CPC ...... A61B 2090/0801; A61B 17/32053; A61B 2017/00367
USPC .......................................... 227/175.1–182.1
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,033,552 A * | 7/1991 | Hu .......................... B25F 3/00 241/37.5 |
| 5,042,707 A | 8/1991 | Taheri |
| 5,047,039 A | 9/1991 | Avant et al. |
| 5,088,173 A | 2/1992 | Kromer et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |

(56) References Cited

U.S. PATENT DOCUMENTS

| | | |
|---|---|---|
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,475,480 B2 * | 1/2009 | Votolato ............... B26B 5/00 30/294 |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,575,144 B2 * | 8/2009 | Ortiz ............... A61B 17/07207 227/19 |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |

(56) References Cited

U.S. PATENT DOCUMENTS

| | | |
|---|---|---|
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,537 B2 * | 12/2010 | Shelton, IV ......... A61B 17/068 227/19 |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,954,682 B2 * | 6/2011 | Giordano ......... A61B 17/07207 227/181.1 |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,628,467 B2 * | 1/2014 | Whitman ............. A61B 17/115 600/129 |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |

(56) References Cited

U.S. PATENT DOCUMENTS

| | | |
|---|---|---|
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,757,133 B2 * | 9/2017 | Latimer .............. A61B 17/064 |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 * | 12/2019 | Sgroi, Jr. .......... A61B 17/07207 |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 10,952,734 B2 * | 3/2021 | Williams .......... A61B 17/1155 |
| 2003/0111507 A1 | 6/2003 | Nunez |
| 2005/0051597 A1 | 3/2005 | Toledano |
| 2005/0100867 A1 * | 5/2005 | Hilscher .............. A61C 17/221 15/22.1 |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0255413 A1 * | 10/2008 | Zemlok .............. A61B 17/1155 600/106 |
| 2008/0281336 A1 * | 11/2008 | Zergiebel .............. A61B 17/068 606/142 |
| 2009/0101694 A1 * | 4/2009 | Marczyk .............. A61B 17/068 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0032179 A1 * | 2/2010 | Hanspers .................. B25F 5/00 173/11 |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |

(56) References Cited

U.S. PATENT DOCUMENTS

| | | | |
|---|---|---|---|
| 2010/0301098 A1* | 12/2010 | Kostrzewski | A61B 17/072 227/176.1 |
| 2011/0011916 A1 | 1/2011 | Levine | |
| 2011/0022032 A1* | 1/2011 | Zemlok | A61B 17/07207 606/1 |
| 2011/0062211 A1* | 3/2011 | Ross | A61B 17/07207 227/175.1 |
| 2011/0114697 A1 | 5/2011 | Baxter, III et al. | |
| 2011/0114700 A1 | 5/2011 | Baxter, III et al. | |
| 2011/0144640 A1 | 6/2011 | Heinrich et al. | |
| 2011/0174099 A1* | 7/2011 | Ross | A61B 17/115 74/89.32 |
| 2011/0192882 A1 | 8/2011 | Hess et al. | |
| 2012/0089131 A1* | 4/2012 | Zemlok | A61B 17/115 606/1 |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0060258 A1 | 3/2013 | Giacomantonio | |
| 2013/0105544 A1 | 5/2013 | Mozdzierz et al. | |
| 2013/0105551 A1 | 5/2013 | Zingman | |
| 2013/0126580 A1 | 5/2013 | Smith et al. | |
| 2013/0153631 A1 | 6/2013 | Vasudevan et al. | |
| 2013/0175315 A1 | 7/2013 | Milliman | |
| 2013/0175318 A1 | 7/2013 | Felder et al. | |
| 2013/0181035 A1 | 7/2013 | Milliman | |
| 2013/0181036 A1 | 7/2013 | Olson et al. | |
| 2013/0193190 A1 | 8/2013 | Carter et al. | |
| 2013/0200131 A1 | 8/2013 | Racenet et al. | |
| 2013/0206816 A1 | 8/2013 | Penna | |
| 2013/0240597 A1 | 9/2013 | Milliman et al. | |
| 2013/0277411 A1 | 10/2013 | Hodgkinson et al. | |
| 2013/0284792 A1 | 10/2013 | Ma | |
| 2013/0334281 A1* | 12/2013 | Williams | A61B 17/07207 227/176.1 |
| 2014/0008413 A1 | 1/2014 | Williams | |
| 2014/0025046 A1* | 1/2014 | Williams | A61B 17/07207 606/1 |
| 2014/0046352 A1 | 2/2014 | Reboa et al. | |
| 2014/0158747 A1 | 6/2014 | Measamer et al. | |
| 2014/0284370 A1 | 9/2014 | Sahin | |
| 2014/0332243 A1* | 11/2014 | Baskar | B25F 5/02 173/29 |
| 2014/0373652 A1* | 12/2014 | Zergiebel | A61B 90/00 74/89.23 |
| 2015/0014393 A1* | 1/2015 | Milliman | A61B 17/1155 227/176.1 |
| 2015/0048140 A1* | 2/2015 | Penna | H01R 12/57 227/176.1 |
| 2015/0053749 A1* | 2/2015 | Shelton, IV | A61B 90/90 227/181.1 |
| 2015/0076205 A1* | 3/2015 | Zergiebel | A61B 17/07207 227/175.1 |
| 2015/0083772 A1 | 3/2015 | Miller et al. | |
| 2015/0173763 A1 | 6/2015 | Liu | |
| 2015/0209045 A1 | 7/2015 | Hodgkinson et al. | |
| 2015/0216525 A1* | 8/2015 | Collins | A61B 90/98 227/176.1 |
| 2015/0343583 A1* | 12/2015 | McRoberts | B23Q 5/045 173/213 |
| 2016/0022267 A1* | 1/2016 | Milliman | A61B 17/1155 227/181.1 |
| 2016/0242779 A1* | 8/2016 | Aranyi | A61B 17/068 |
| 2016/0270835 A1* | 9/2016 | Reed | A61B 17/8883 |
| 2016/0374669 A1* | 12/2016 | Overmyer | A61B 17/1155 227/176.1 |
| 2017/0265857 A1* | 9/2017 | Williams | A61B 17/115 |
| 2018/0125495 A1* | 5/2018 | Sgroi, Jr. | A61B 17/07207 |
| 2018/0360460 A1* | 12/2018 | Mozdzierz | A61B 17/3476 |
| 2020/0276693 A1* | 9/2020 | Sgroi, Jr. | B25C 5/1617 |

FOREIGN PATENT DOCUMENTS

| | | | | |
|---|---|---|---|---|
| CA | 2805365 | A1 | 8/2013 | |
| CN | 104039244 | A | 9/2014 | |
| CN | 104042288 | A | 9/2014 | |
| CN | 104367360 | A | 2/2015 | |
| DE | 1057729 | B | 5/1959 | |
| DE | 3301713 | A1 | 7/1984 | |
| EP | 0152382 | A2 | 8/1985 | |
| EP | 0173451 | A1 | 3/1986 | |
| EP | 0190022 | A2 | 8/1986 | |
| EP | 0282157 | A1 | 9/1988 | |
| EP | 0503689 | A2 | 9/1992 | |
| EP | 1175868 | B1 * | 7/2003 | A61B 17/115 |
| EP | 1354560 | A2 | 10/2003 | |
| EP | 2138118 | A2 | 12/2009 | |
| EP | 2168510 | A1 | 3/2010 | |
| EP | 2238926 | A2 | 10/2010 | |
| EP | 2524656 | A2 | 11/2012 | |
| FR | 1136020 | A | 5/1957 | |
| FR | 1461464 | A | 2/1966 | |
| FR | 1588250 | A | 4/1970 | |
| FR | 2443239 | A1 | 7/1980 | |
| GB | 1185292 | A | 3/1970 | |
| GB | 2016991 | A | 9/1979 | |
| GB | 2070499 | A | 9/1981 | |
| JP | 2004147969 | A | 5/2004 | |
| JP | 2013138860 | A | 7/2013 | |
| NL | 7711347 | A | 4/1979 | |
| SU | 1509052 | A1 | 9/1989 | |
| WO | 8706448 | A1 | 11/1987 | |
| WO | 8900406 | A1 | 1/1989 | |
| WO | 9006085 | A1 | 6/1990 | |
| WO | 98/35614 | A1 | 8/1998 | |
| WO | 0154594 | A1 | 8/2001 | |
| WO | 02080781 | A2 | 10/2002 | |
| WO | 2008107918 | A1 | 9/2008 | |

* cited by examiner

STAPLE RELOAD ASSEMBLY WITH RELEASABLE KNIFE

CROSS-REFERENCE TO RELATED APPLICATIONS

This application claims the benefit of and priority to U.S. Provisional Patent Application Ser. No. 62/981,636 filed Feb. 26, 2020, the entire disclosure of which is incorporated by reference herein.

FIELD

This disclosure is generally related to surgical stapling devices and, more particularly, to circular surgical stapling devices that include a knife to cut tissue.

BACKGROUND

Circular stapling devices typically include a shell or reload assembly that has a staple cartridge, a staple pusher, and an annular knife. The staple cartridge supports one or more annular rows of staples, and the staple pusher is movable within the staple cartridge to eject the staples from the staple cartridge. The annular knife is positioned radially inward of the annular rows of staples and is movable from a retracted position to an advanced position to cut or core tissue. The annular knife can be movable simultaneously with the staple pusher or independently of the staple pusher to cut tissue during a surgical procedure, e.g., an anastomosis procedure.

During an anastomosis procedure, two tubular sections of tissue are attached to one another and the tissues within the tubular sections are cored with the knife to define a hollow passage between the joined tubular sections. Generally, a tissue donut remains within the annular knife of the reload assembly after the tissue sections have been cut. When the reload assembly is removed from a patient, the tissue donut is removed from within the annular knife by the clinician.

After a circular stapling device is actuated to cut tissue during an anastomosis procedure, the knife is moved from an advanced position in which a cutting edge of the annular knife is exposed to a retracted position in which the cutting edge of the knife is recessed within the staple cartridge of the reload assembly and shielded. During removal of the tissue donut from within the annular knife, the cutting edge of the knife is pulled in a distal direction which may inadvertently expose the cutting edge of the knife. Exposure of the cutting edge of the knife presents a danger to the clinician handling the stapling device.

SUMMARY

The techniques of this disclosure generally relate to circular stapling devices having a knife to cut tissue. In aspects of the disclosure, the surgical stapling device includes an anvil assembly and a reload assembly that includes a knife and a knife carrier. The knife is releasably coupled to the knife carrier and is embedded in a cut ring of the anvil assembly when the stapling device is fired. The knife is separable from the knife carrier upon application of a predetermined force on the knife. The predetermined force is applied to the knife after the stapling device is fired by moving the anvil assembly in relation to the reload assembly from a clamped position to an open position.

One aspect of the disclosure is directed to a reload assembly including a shell housing, a staple cartridge, a staple pushing member, a knife carrier, and a knife. The shell housing defines a cavity and has a proximal portion and a distal portion. The staple cartridge is supported on the distal portion of the shell housing and supports a plurality of staples. The staple pushing member is movable within the shell housing between an advanced position and a retracted position to eject the plurality of staples from the staple cartridge. The staple pushing member defines a longitudinal bore. The knife carrier is supported within the longitudinal bore of the staple pushing member and has a distal portion defining a first engagement portion. The knife carrier is movable between retracted and advanced positions within the shell housing. The knife has a proximal portion and a distal portion. The proximal portion defines a second engagement portion that is coupled to the first engagement portion to releasably secure the knife to the knife carrier. The knife can be uncoupled from the first engagement portion of the knife carrier upon application of a predetermined force to the knife in a distal direction.

In aspects of the disclosure, the knife is annular.

In some aspects of the disclosure, the first engagement portion is defined by a plurality of resilient fingers formed on the distal portion of the knife carrier.

In certain aspects of the disclosure, each of plurality of resilient fingers defines a concave surface to define an annular recess about the distal portion of the knife carrier.

In aspects of the disclosure, the second engagement portion is formed on the proximal portion of the knife and includes an annular convex portion that is received within the annular recess defined by the plurality of resilient fingers of the knife carrier to releasably secure the knife to the knife carrier.

In aspects of the disclosure, the second engagement portion is formed on the proximal portion of the knife by inverting the proximal portion of the knife.

Another aspect of the disclosure is directed to a stapling device including an adaptor assembly, a reload assembly, and an anvil assembly. The adaptor assembly has a distal end portion. The reload assembly is secured to the distal end portion of the adaptor assembly and includes a shell housing, a staple cartridge assembly, a staple pushing member, a knife carrier, and a knife. The shell housing defines a cavity and has a proximal portion and a distal portion. The staple cartridge is supported on the distal portion of the shell housing and supports a plurality of staples. The staple pushing member is movable within the shell housing between an advanced position and a retracted position to eject the plurality of staples from the staple cartridge. The staple pushing member defines a longitudinal bore. The knife carrier is supported within the longitudinal bore of the staple pushing member and has a distal portion defining a first engagement portion. The knife carrier is movable between retracted and advanced positions within the shell housing. The knife has a proximal portion and a distal portion. The distal portion defines a cutting edge. The proximal portion defines a second engagement portion that is coupled to the first engagement portion to releasably secure the knife to the knife carrier. The knife can be uncoupled from the first engagement portion of the knife carrier upon application of a predetermined force to the knife in a distal direction. The anvil assembly is movable in relation to the staple cartridge between an open position and a clamped position and includes a cut ring formed of a material penetrable by the knife. The knife is embedded in the cut ring when the stapling device is fired and is separated from the knife carrier after the stapling device is fired upon movement of the anvil assembly from the clamped position to the open position.

Another aspect of the disclosure is directed to a knife assembly including a knife carrier and a knife. The knife carrier has a distal portion defining a first engagement portion. The knife has a proximal portion and a distal portion. The distal portion defines a cutting edge. The proximal portion defines a second engagement portion that is coupled to the first engagement portion to releasably secure the knife to the knife carrier. The knife can be uncoupled from the first engagement portion of the knife carrier upon application of a predetermined force to the knife.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Various aspects and features of the disclosure are described with reference to the drawings wherein like numerals designate identical or corresponding elements in each of the several views and.

DETAILED DESCRIPTION

Figure 1:
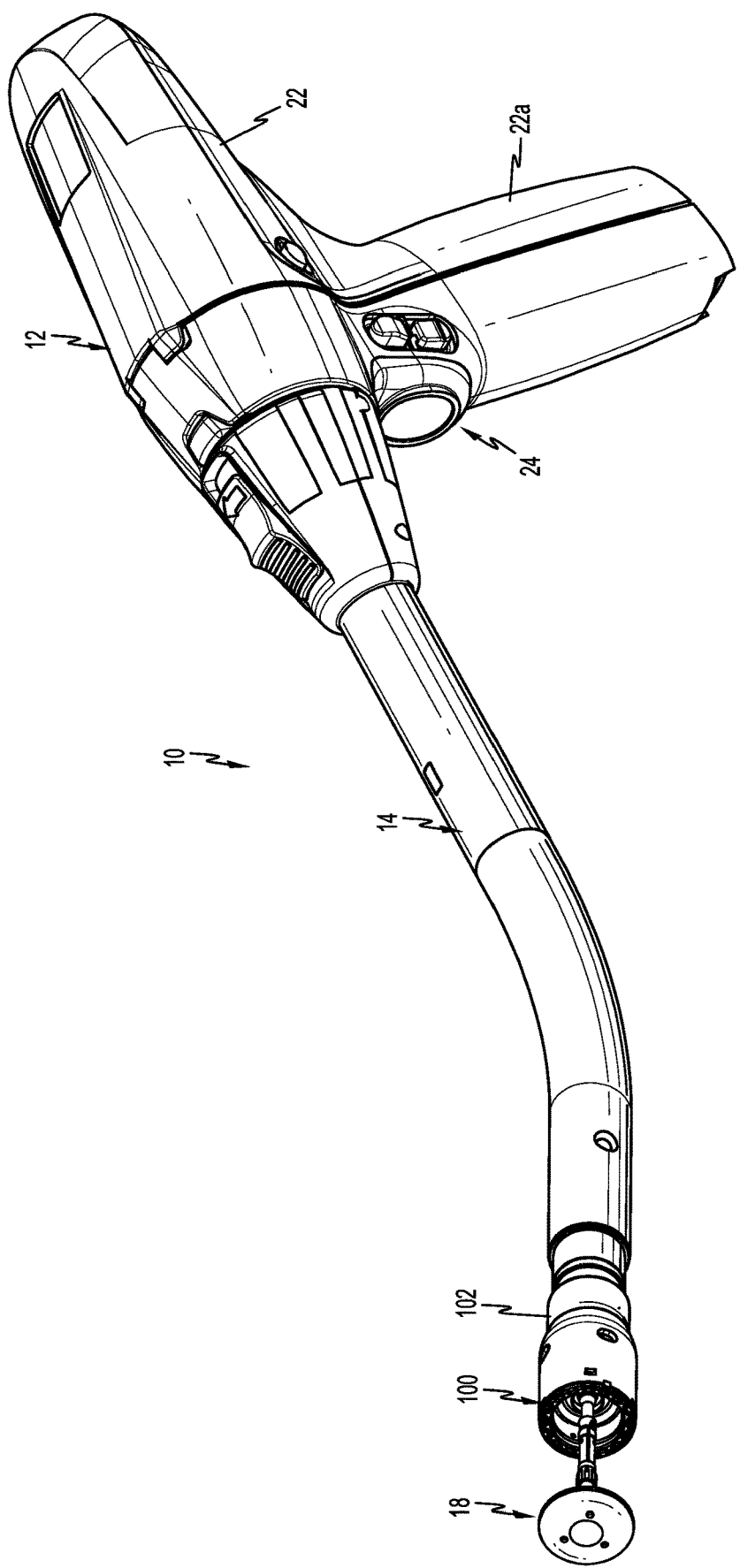
FIG. 1 is a side perspective view of a surgical stapling device including a tool assembly having a reload assembly in accordance with aspects of the disclosure.

The disclosed surgical stapling device including a reload assembly including various aspects of the disclosure will now be described in detail with reference to the drawings in which like reference numerals designate identical or corresponding elements in each of the several views. However, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. Further, the term "clinician" is used generally to refer to medical personnel including doctors, nurses, and support personnel.

This disclosure is directed to a circular surgical stapling device that includes a reload assembly having a knife carrier that is releasably coupled to a knife having a cutting edge and can be separated from the knife carrier upon application of a predetermined force to the knife. The knife is positioned to engage and penetrate a cut ring assembly on an anvil assembly of the stapling device when the stapling device is fired. Engagement of the knife with the cut ring assembly is sufficient to disengage the knife from the knife carrier when the knife carrier returned to a retracted position after the stapling device has been fired. When the knife disengages from the knife carrier, a cutting edge of the knife is embedded in the cut ring assembly to shield the cutting edge of the knife from a clinician.

Figure 10:
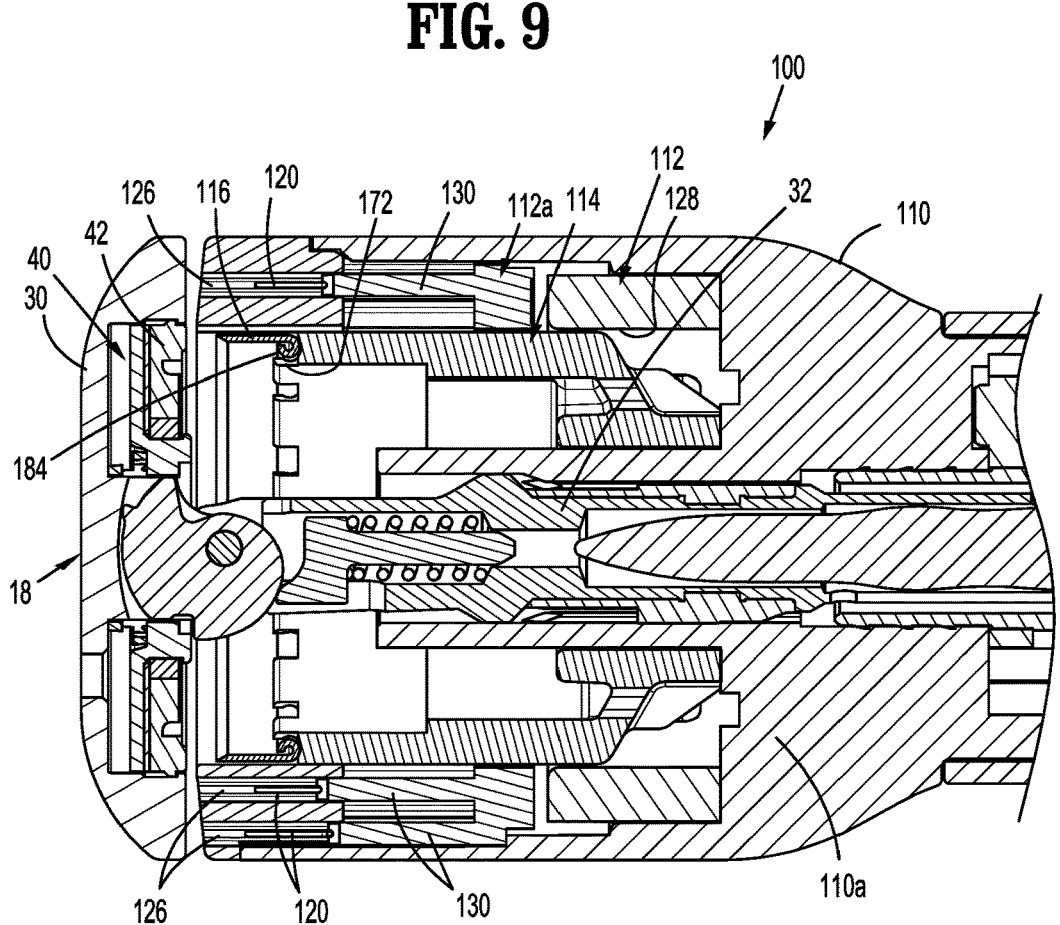
FIG. 10 is a cross-sectional view taken along section line 10-10 of FIG. 2 with the surgical stapling device in a clamped position.

FIG. 1 illustrates a circular stapling device 10 including a reload assembly in accordance with aspects of the disclosure shown generally as a reload assembly 100. The circular stapling device 10 includes a handle or actuator assembly 12, an elongate body or adaptor assembly 14, the reload assembly 100, and an anvil assembly 18 that is supported for movement in relation to the reload assembly 100 between an unclamped position and a clamped position (FIG. 10). In aspects of the disclosure, the reload assembly 100 includes a proximal portion 102 that is releasably coupled to a distal portion of the adaptor assembly 14 and the adaptor assembly 14 includes a proximal portion that is releasably coupled to the handle assembly 12. Alternately, it is envisioned that the reload assembly 100 can be fixedly secured to the adaptor assembly 14 and/or the adaptor assembly can be fixedly secured to the handle assembly 12. The handle assembly 12 includes a body 22 that defines a stationary hand grip 22*a* that supports actuation buttons 24 for controlling operation of various functions of the circular stapling device 10 including approximation of the reload assembly 100 and anvil assembly 18, firing of staples from the reload assembly 100, and cutting or coring of tissue as described in further detail below.

The circular stapling device 10 is illustrated as an electrically powered stapling device including an electrically powered handle assembly 12 that may support one or more batteries (not shown). The adaptor assembly 14 translates power from the handle assembly 12 to the reload and anvil assemblies 100, 18, respectively, to staple and cut tissue. Examples of electrically powered stapling devices can be found in U.S. Pat. Nos. 9,055,943, 9,023,014, and U.S. Publication Nos. 2018/0125495, and 2017/0340351. Alternately, it is envisioned that aspects of the reload assembly 100 disclosed herein could also be incorporated into a manually powered stapling device such as disclosed in, e.g., U.S. Pat. No. 7,303,106 (the '106 Patent), or a stapling device that is configured for use with a robotic system as disclosed in, e.g., U.S. Pat. No. 9,962,159, that does not include a handle assembly.

Figure 2:
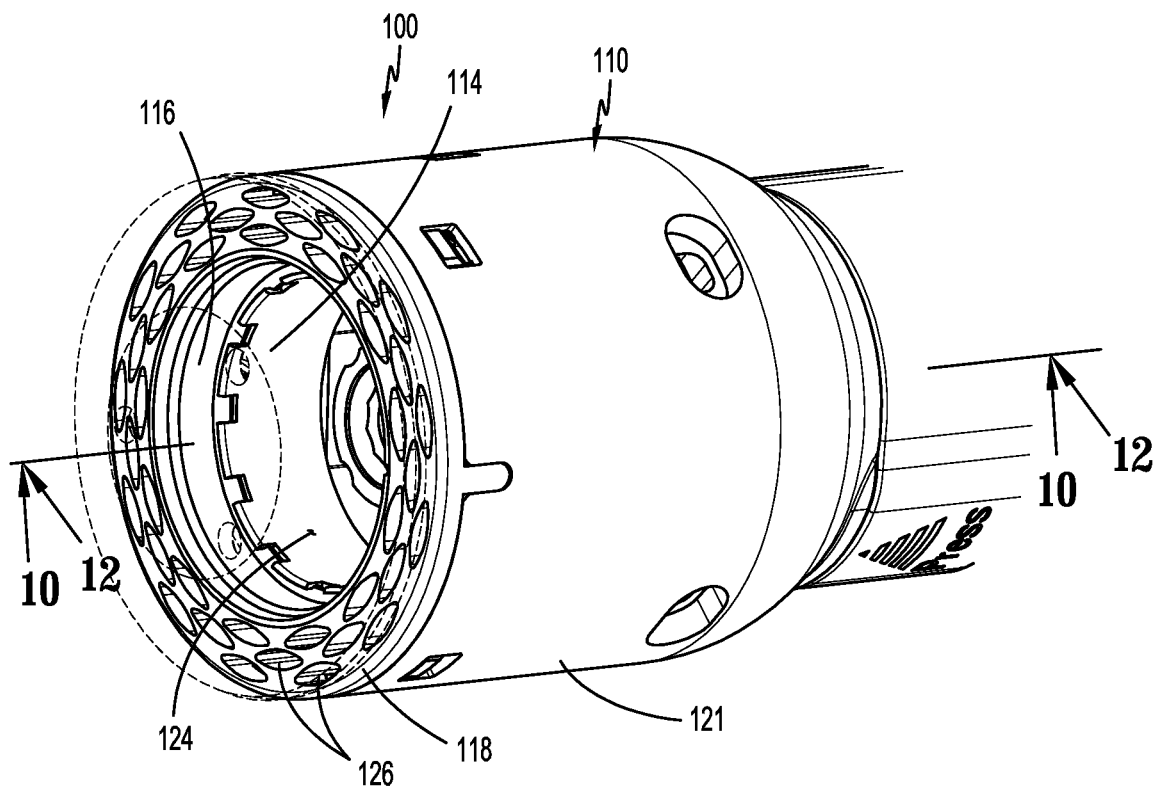
FIG. 2 is an enlarged view of a distal portion of the surgical stapling device shown in FIG. 1 with an anvil assembly removed.
Figure 3:
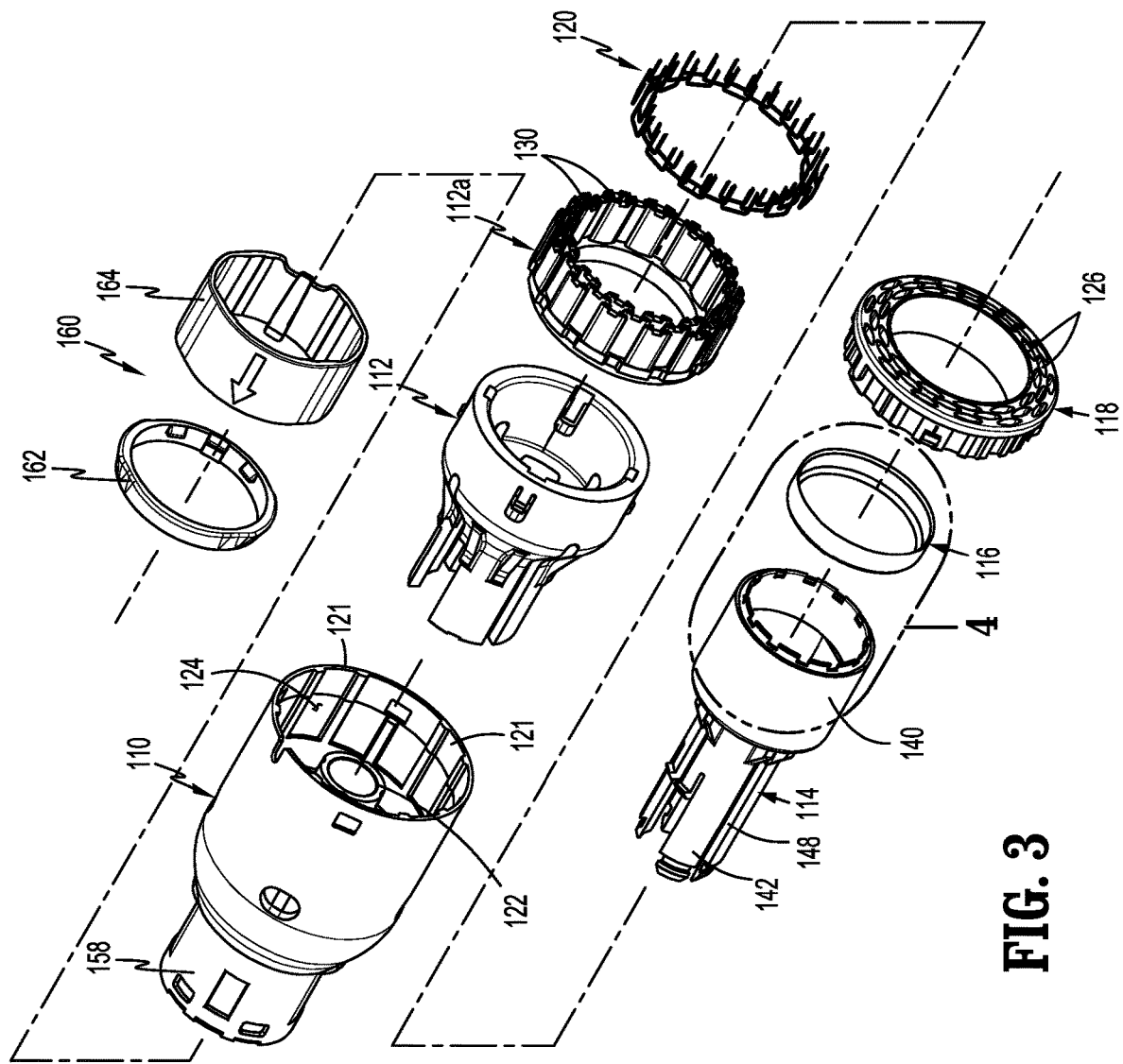
FIG. 3 is a side perspective exploded view of the reload assembly of the surgical stapling device of FIG. 1.

FIGS. 2 and 3 illustrate the reload assembly 100 which includes a shell housing 110, a staple actuator 112, a staple pushing member 112*a*, a knife carrier 114, an annular knife 116 supported on the knife carrier 114, a staple cartridge 118, and a plurality of staples 120 supported within the staple cartridge 118. The shell housing 110 includes an outer housing portion 121 and an inner housing portion 122 that are spaced from each other to define an annular cavity 124. The staple actuator 112 and the staple pushing member 112*a* are movable within the annular cavity 124 of the shell housing 110 from a retracted position to an advanced position to eject the staples 120 from the staple cartridge 118.

The staple cartridge 118 is annular and defines annular rows of staple pockets 126. Each of the staple pockets 126 supports one of the staples 120. The staple actuator 112 and the staple pushing member 112*a* define a longitudinal through bore 128 (FIG. 10) that receives the knife carrier 114. The staple actuator 112 has a distal portion that abuts a proximal portion of the staple pushing member 112*a* such that distal movement of the staple actuator 112 within the shell housing 110 causes distal movement of the staple pushing member 112*a* within the shell housing 110. The staple pushing member 112*a* of the reload assembly 100 has a plurality of fingers 130 (FIG. 3). Each of the plurality of fingers 130 is received within a respective one of the staple pockets 126 of the staple cartridge 118 and is movable through the respective staple pocket 126 to eject the staples 120 from the staple pockets 126 when the staple pushing member 112*a* is moved from a retracted position (FIG. 10) to an advanced position (FIG. 11) within the shell housing 110.

Figure 11:
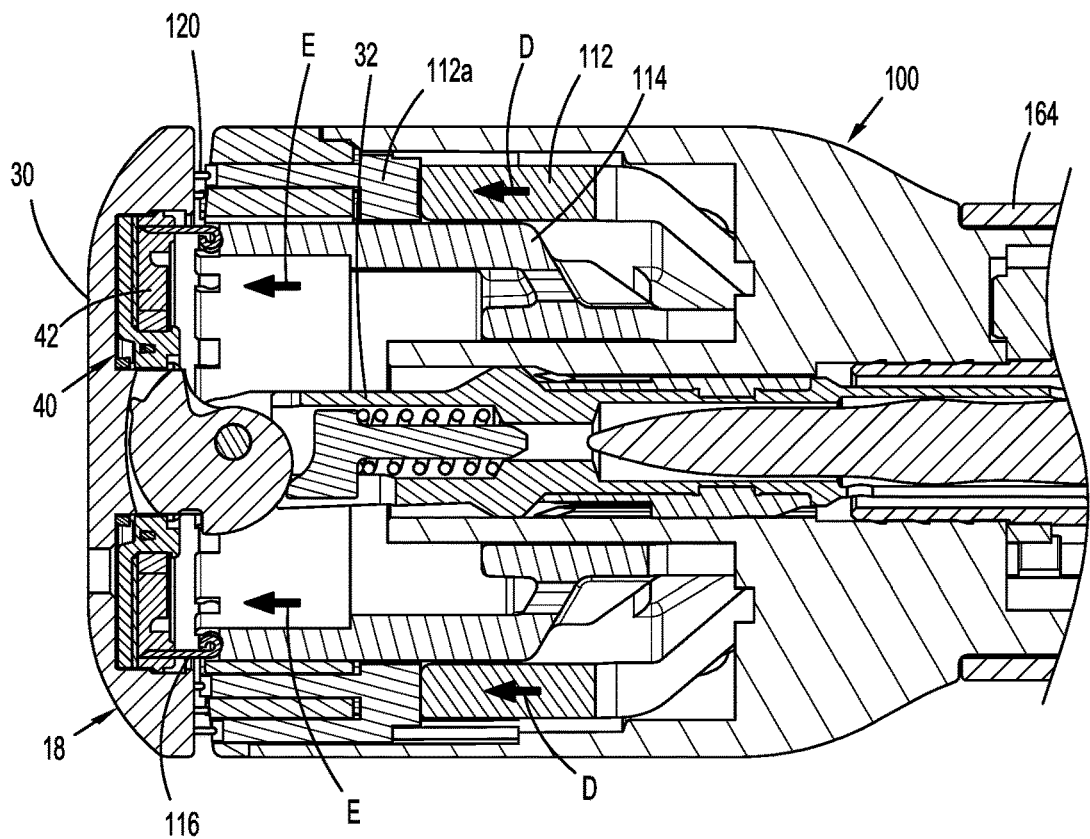
FIG. 11 is a cross-sectional view taken along section line 11-11 of FIG. 2 with the surgical stapling device in a clamped and fired position.

The knife carrier 114 is received within the longitudinal through bore 128 of the staple actuator 112 and includes a distal portion 140 and a plurality of spaced longitudinally extending proximal portions 142 (FIG. 3). The distal portion 140 and the proximal portions 142 define a stepped central bore that receives the inner housing portion 122 (FIG. 3) of the shell housing 110 such that the knife carrier 114 is movable within the staple actuator 112 about the inner housing portion 122 of the shell housing 110 between a retracted position (FIG. 10) and an advanced position (FIG. 11). The proximal portions 142 of the knife carrier 114 defines slots 148 that receive guide portions 110*a* of the shell housing 110 to limit the knife carrier 114 to longitudinal movement within the shell housing 110.

The shell housing 110 includes a proximal portion 158 that supports a coupling mechanism 160 (FIG. 3) that releasably couples the reload assembly 100 to the adaptor assembly 14 of the stapling device 10 (FIG. 1) to facilitate replacement of the reload assembly 100 and reuse of the stapling device 10. The coupling mechanism 160 includes a retaining member 162 and a coupling member 164. The retaining member 162 secures the coupling member 164 about the proximal portion 158 of the shell housing 110. The coupling member 164 is received about the proximal portion 158 of the shell housing 110 and engages the distal portion 14*a* (FIG. 1) of the adaptor assembly 14 to couple the adaptor assembly 14 to the reload assembly 100. It is envisioned that other coupling mechanisms can be used to secure the reload assembly 100 to the adaptor 14.

Figure 4:
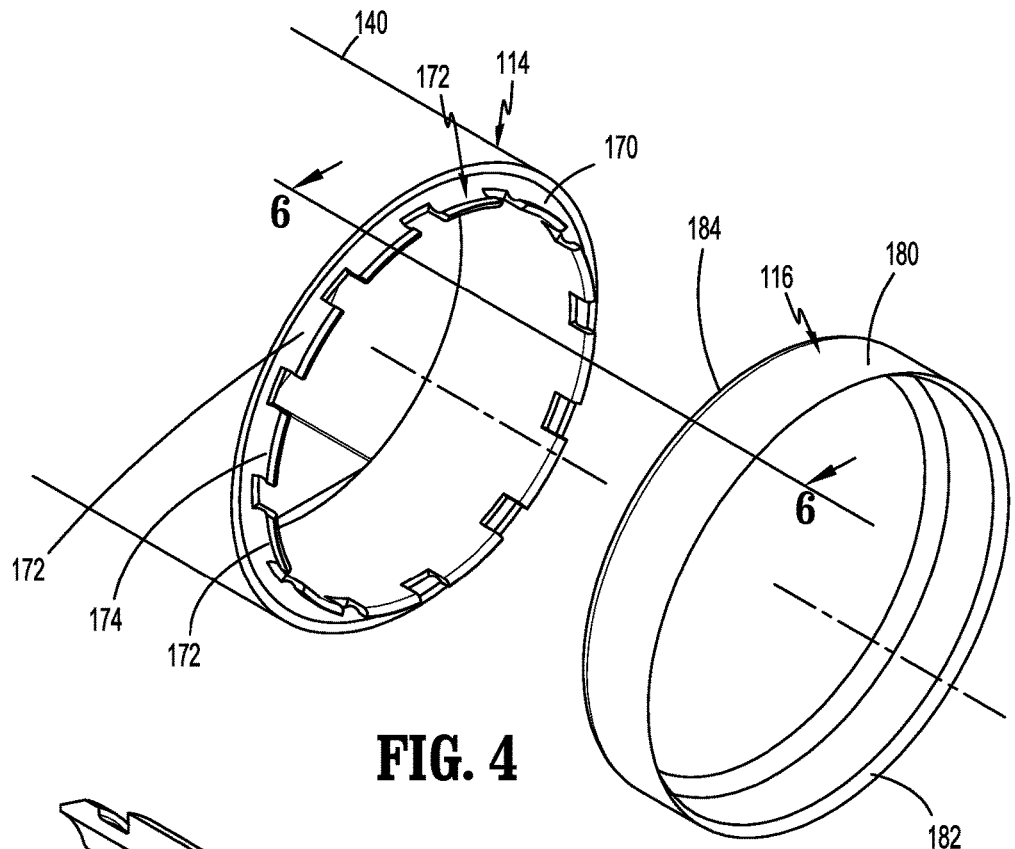
FIG. 4 is an enlarged view of the indicated area of detail shown in FIG. 3.
Figure 5:
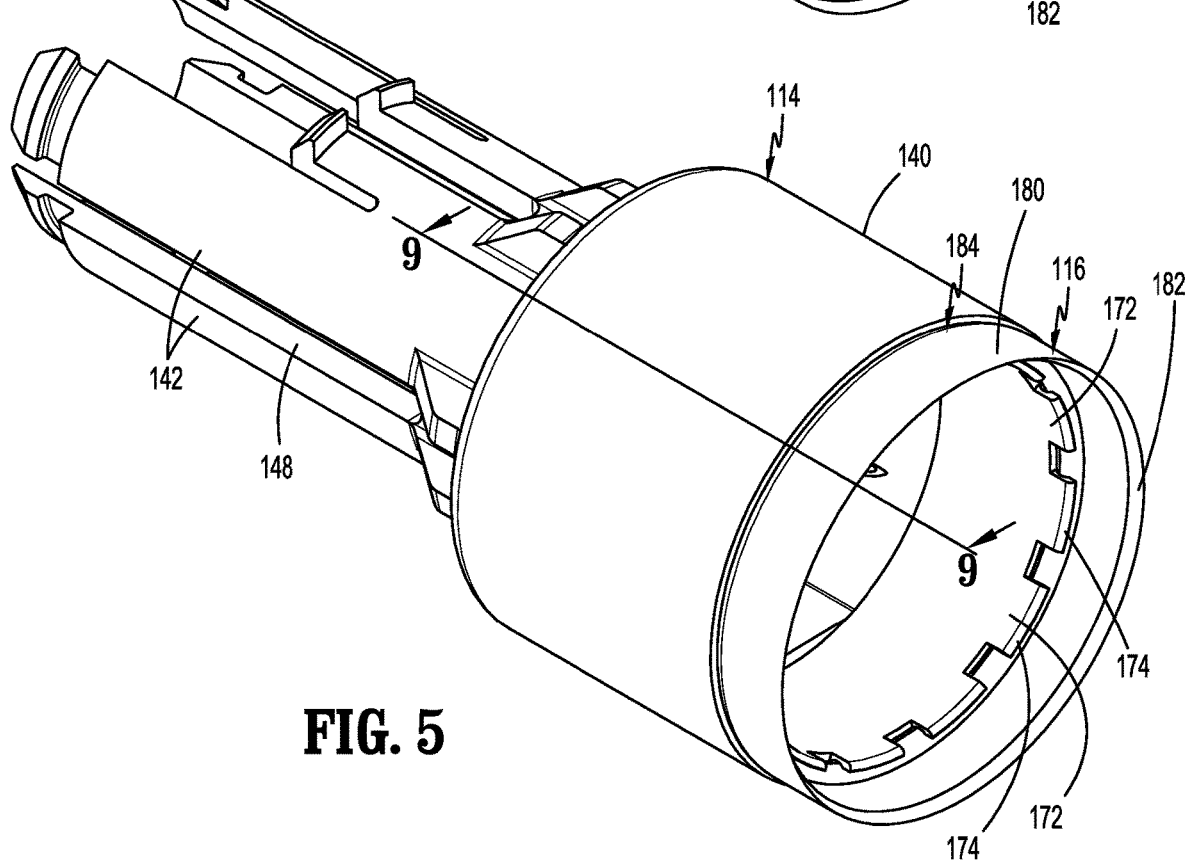
FIG. 5 is a side perspective view of the knife carrier and annular knife of the surgical stapling device shown in FIG. 3
Figure 6:
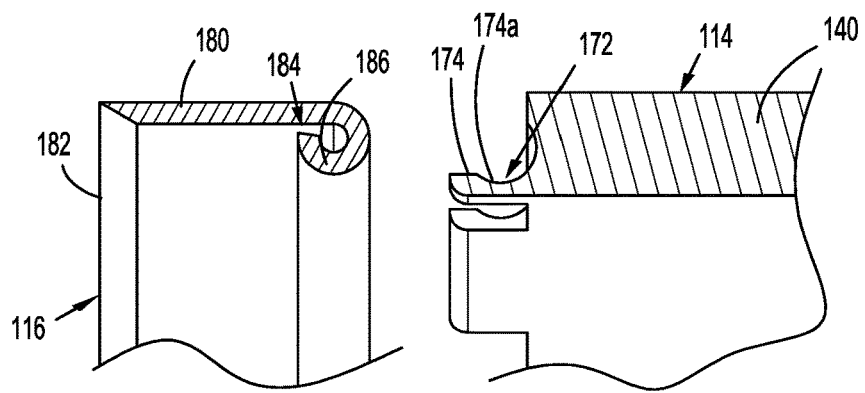
FIG. 6 is a cross-sectional view taken along section line 6-6 of FIG. 4 with the annular knife separated from the knife carrier.

FIGS. 4-6 illustrate the distal portion 140 of the knife carrier 114 and the annular knife 116 of the reload assembly 100. The distal portion 140 of the knife carrier 114 is substantially cylindrical and includes an area of reduced diameter 170. In aspects of the disclosure, the area of reduced diameter 170 is defined in part by a plurality of resilient fingers or detents 172. Each of the plurality of resilient fingers 172 includes an engagement portion 174 that releasably engages the annular knife 116 to secure the annular knife 116 to the knife carrier 114. In certain aspects of the disclosure, the engagement portion 174 of each of the resilient fingers 172 defines an outwardly facing concave surface 174*a* such that the area of reduced diameter 170 on the distal portion 140 of the knife carrier 114 defines an annular recess.

The annular knife 116 includes a body 180 that has an annular cutting edge 182 at its distal end and an engagement portion 184 on its proximal end portion. In aspects of the disclosure, the engagement portion 184 on the proximal end of the annular knife 116 includes an annular or substantially annular convex portion 186 (FIG. 6) that is received within the annular recess defined by the engagement portion 174 of the resilient fingers 172 to releasably secure the annular knife 116 to the distal portion 140 of the knife carrier 114. In certain aspects of the disclosure, the engagement portion 184 on the proximal end portion of the annular knife 116 is formed by curling or inverting the proximal end portion of the annular knife 116 inwardly upon itself.

Figure 7:
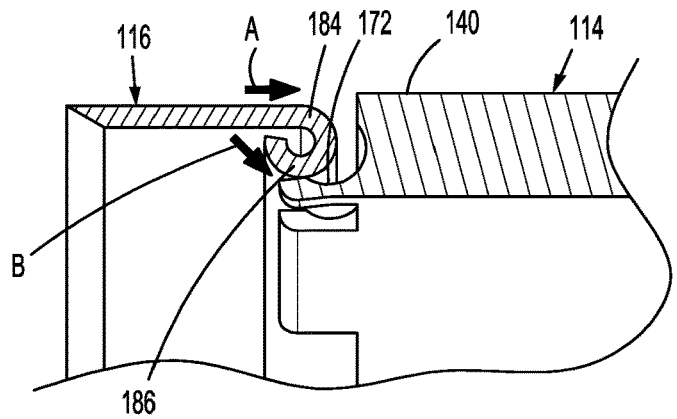
FIG. 7 is a cross-sectional cutaway view through a distal portion of the knife carrier and the annular knife as the annular knife is moved into engagement with the knife carrier.
Figure 8:
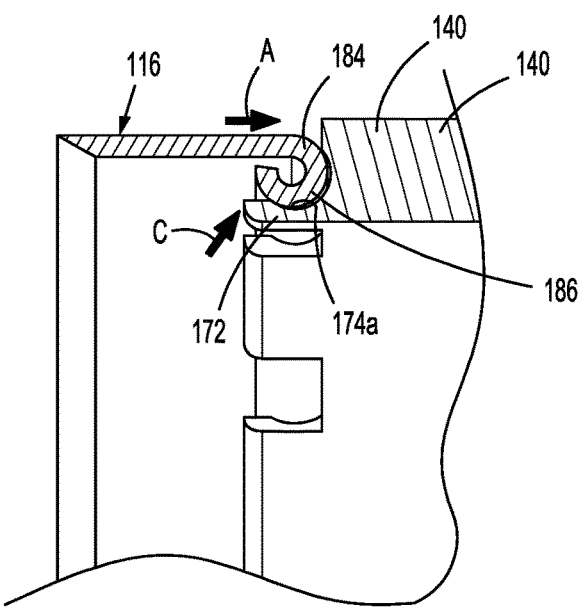
FIG. 8 is a cross-sectional cutaway view through the distal portion of the knife carrier and the annular knife with the annular knife engaged with the knife carrier.
Figure 9:
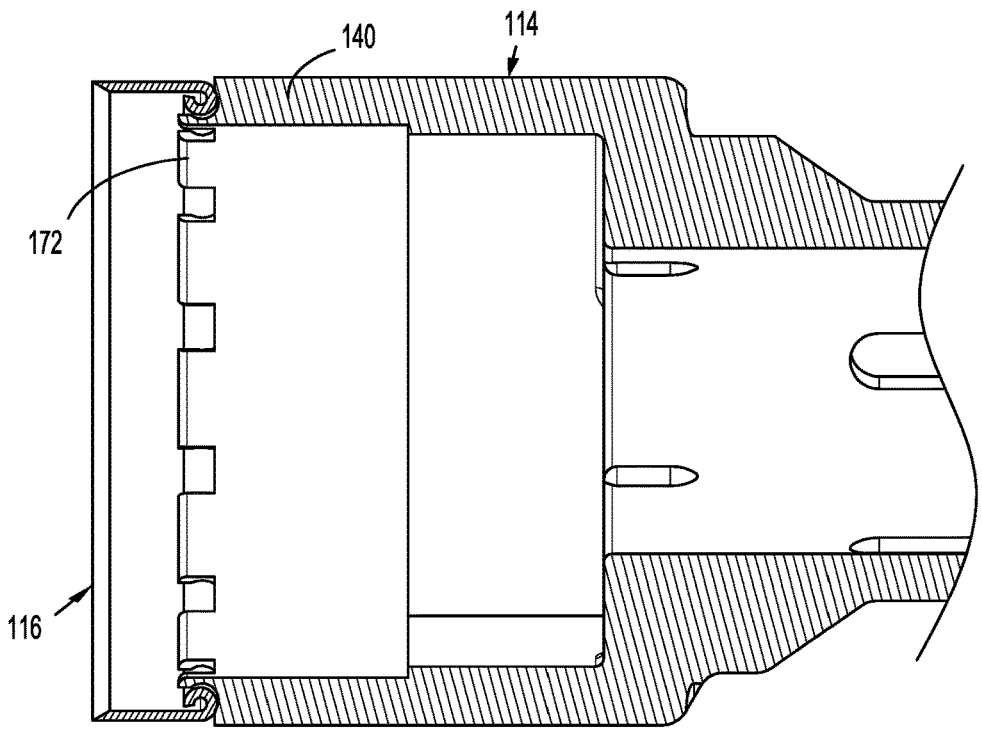
FIG. 9 is a cross-sectional view through the distal portion of the knife carrier and the annular knife with the annular knife engaged with the knife carrier.

FIGS. 7-9 illustrate the annular knife 116 as the annular knife 116 is coupled to the distal portion 140 of the knife carrier 114. In order to couple the annular knife 116 to the knife carrier 114, the proximal end portion of the annular knife 116 is aligned with the distal portion 140 of the knife carrier 114 and the annular knife 116 is moved in the direction indicated by arrow "A" in FIG. 7 towards the knife carrier 114. When the engagement portion 184 on the proximal end portion of the annular knife 116 engages the resilient fingers 172 on the distal portion 184 of the knife carrier 114, the resilient fingers 172 are deformed inwardly in the direction indicated by arrow "B" in FIG. 7 to allow the engagement portion 184 on the proximal end of the annular knife 116 to pass over the resilient fingers 172 and into the annular recess defined by the concave surfaces 174*a* of the resilient fingers 172. When the engagement portion 184 of the annular knife 116 passes over the resilient fingers 172 and into the annular recess defined by the resilient fingers 172, the resilient fingers 172 return to their non-deformed positions in the direction of arrow "C" in FIG. 8 to retain the annular knife 116 on the distal portion of the knife carrier 114. The annular knife 116 will remain on the distal portion of the knife carrier 114 until a pre-determined force is applied to the annular knife 116 sufficient to disengage the engagement portion 184 on the proximal end of the annular knife 116 from within the annular recess defined by the concave surfaces 174a of the resilient fingers 172. The pre-determined force can be set to a desirable level by selecting a material used to form fingers 172 of the knife carrier 114 having the appropriate resilience and/or thickness.

It is envisioned that the engagement portions of the knife carrier 114 and the annular knife 116 may have a variety of different configurations not shown here that function to releasably couple the annular knife 116 with the knife carrier 114. It is also envisioned that the engagement portions of the annular knife 116 and the knife carrier 114 can be configured to interlock, operate via friction, and/or fracture.

FIG. 10 illustrates the reload assembly 100 and the anvil assembly 18 of the stapling device 10 in the clamped, non-fired position with the staple actuator 112, the stapling pushing member 112a, the knife carrier 114, and the annular knife 116 in their retracted positions and the anvil assembly 18 in juxtaposed alignment with the staple cartridge 118. In this position, the annular cutting edge 182 is recessed within the staple cartridge 118.

Figure 14:
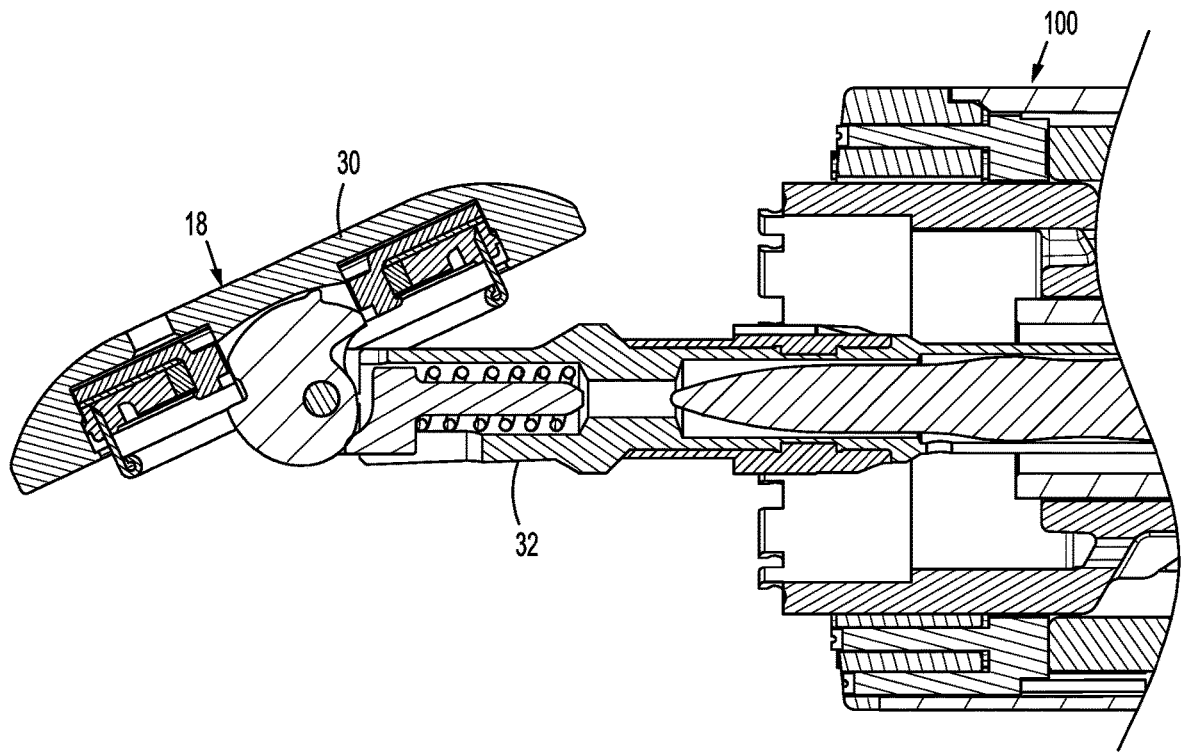
FIG. 14 is a cross-sectional view of the distal portion of the surgical stapling device shown in FIG. 1 with the surgical stapling device in the fired, unclamped position, an anvil assembly in a tilted position, and the annular knife separated from the knife carrier.

As illustrated, the anvil assembly 18 includes an anvil head 30 that is pivotably supported on a center rod 32. The anvil head 30 can pivot on the center rod 32 from an operative position (FIG. 10) to a tilted or reduced profile position (FIG. 14). For a description of the operation of exemplary aspects of an anvil assembly including a tiltable anvil head, see the '106 Patent. The anvil head 30 supports a cut ring assembly 40 that includes a cut ring 42 that is aligned with the cutting edge 182 of the knife 116. The cut ring 42 is formed of a material that can be penetrated by the cutting edge 182 of the knife 116 when the knife 116 is advanced into the cut ring 42 as the stapling device 10 (FIG. 1) is fired.

FIG. 11 illustrates the reload assembly 100 and anvil assembly 18 of the stapling device 10 in the clamped and fired position. In this position, the staple actuator 112 and the stapling pushing member 112a have moved in the direction indicated by arrows "D" to an advanced position to eject the staples 120 from the staple cartridge 118 into the anvil head 30. In addition, the knife carrier 114 and the annular knife 116 which is coupled to the distal portion 140 of the knife carrier 114 have moved in the direction of arrows "E" to their advanced positions to advance the cutting edge 182 of the annular knife 116 into a cut ring 42 of the anvil assembly 18. In this position, the distal portion of the annular knife 116 is embedded in the cut ring 42 of the anvil assembly 18.

Figure 12:
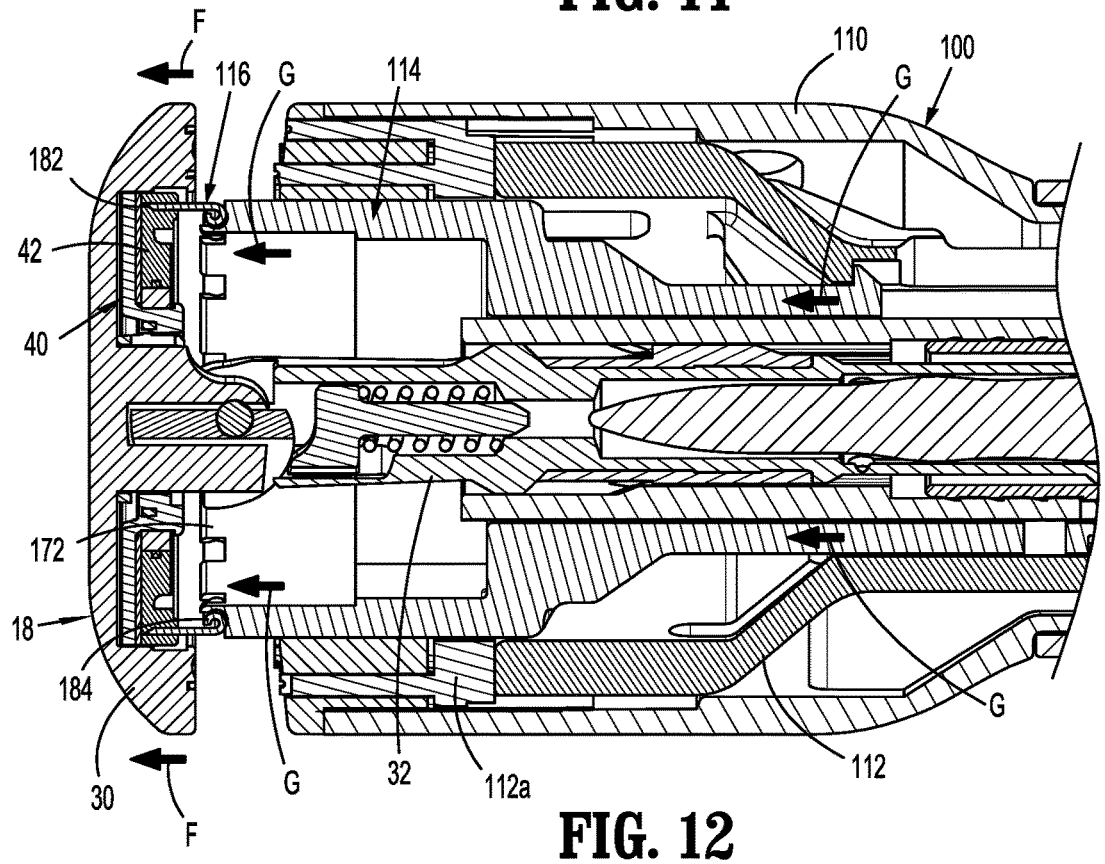
FIG. 12 is a cross-sectional view taken along section line 11-11 of FIG. 2 with the surgical stapling device in the fired position as the surgical stapling device is moved towards an unclamped position.
Figure 13:
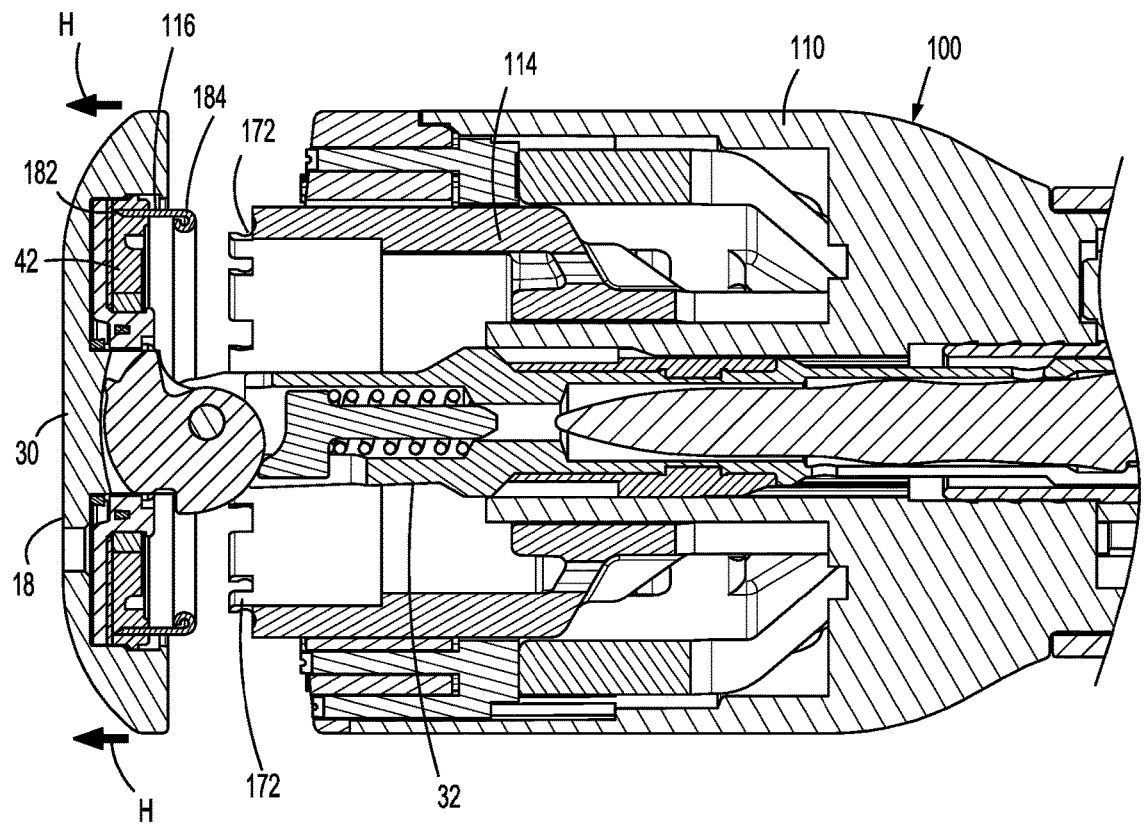
FIG. 13 is a cross-sectional view taken along section line 11-11 of FIG. 2 after the surgical stapling device is fired as the surgical stapling device is moved to an unclamped position and the annular knife is separated from the knife carrier.

FIGS. 12 and 13 illustrate the reload assembly 100 and anvil assembly 18 of the stapling device 10 in the fired position as the anvil assembly 18 is moved from a clamped position in which the anvil head 30 is in juxtaposed alignment with the staple cartridge 118 towards an open position in which the anvil head 30 is spaced from the staple cartridge 118. In this position, the anvil assembly 18 is moved in the direction of arrows "F" away from the knife carrier 114. Since the annular knife 116 is embedded in the cut ring 42 of the anvil head 30, movement of the anvil head 30 in the direction of arrows "F" will move the knife carrier 114 in the direction of arrows "G" as shown in FIG. 12. When the knife carrier 114 is restricted from any further distal movement within the shell housing 110, further distal movement of the anvil head 30 in relation to the knife carrier 114 in the direction of arrows "H" in FIG. 13 will cause the engagement portion 184 on the proximal portion of the annular knife 116 to apply a force on the resilient fingers 172 on the distal end of the knife carrier 114 to disengage the annular knife 116 from the knife carrier 114. The cutting edge 182 of the annular knife 116 will remain embedded in the cut ring 42 of the cut ring assembly 40 in the anvil head 30 of the anvil assembly 18 to safely shield the clinician from the cutting edge 182 of the annular knife 116.

Figure 15:
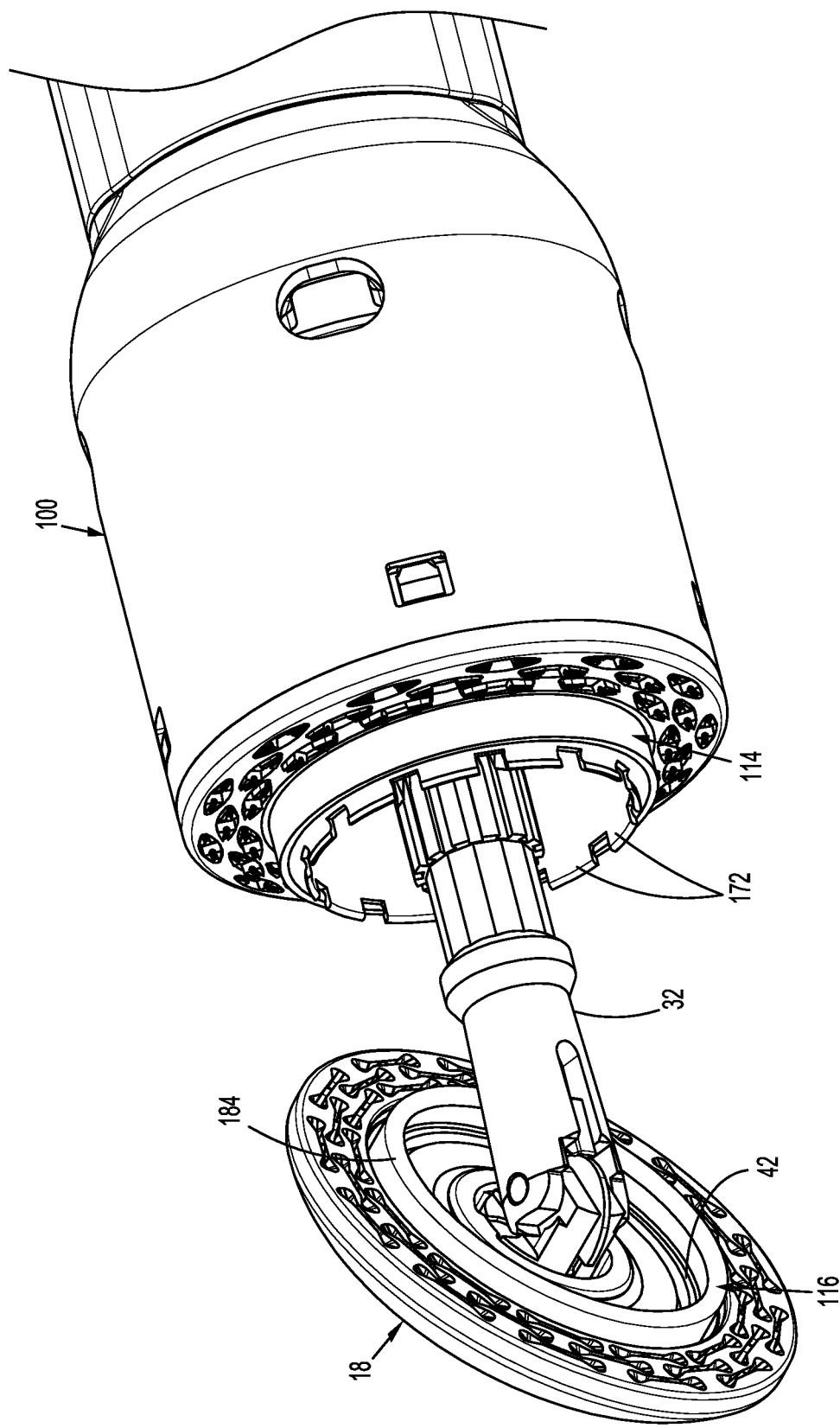
FIG. 15 is a side perspective view of the distal portion of the surgical stapling device shown in FIG. 14 with the surgical stapling device in the unclamped, fired position and the annular knife separated from the knife carrier.

FIGS. 14 and 15 illustrate the reload assembly 100 and the anvil assembly 18 of the stapling device 10 with the anvil head 30 of the anvil assembly 18 in the tilted position and the annular knife 116 embedded in the cut ring 42 of the cut ring assembly 40 of the anvil assembly 18. The anvil head 30 is urged to the tilted position by a biasing mechanism 50 supported within the center rod 32 of the anvil assembly 18. For a detailed description of exemplary aspects of the biasing mechanism 50, see, e.g., the '106 patent.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A reload assembly comprising:
   a shell housing defining a cavity and having a proximal portion and a distal portion;
   a staple cartridge supported on the distal portion of the shell housing, the staple cartridge supporting a plurality of staples;
   a staple pushing member movable within the shell housing between an advanced position and a retracted position to eject the plurality of staples from the staple cartridge, the staple pushing member defining a longitudinal bore;
   a knife carrier supported within the longitudinal bore of the staple pushing member, the knife carrier having a distal portion defining a first engagement portion including a plurality of resilient fingers formed on the distal portion of the knife carrier, each of plurality of resilient fingers having a concave surface to define an annular recess about the distal portion of the knife carrier, the knife carrier movable between retracted and advanced positions within the shell housing; and
   a knife having a proximal portion and a distal portion, the proximal portion defining a second engagement portion that is coupled to the first engagement portion to releasably secure the knife to the knife carrier, wherein one of the first engagement portion or the second engagement portion is formed of a resilient material such that the knife can be uncoupled from the first engagement portion of the knife carrier upon application of a predetermined force to the knife in a distal direction,
   wherein the second engagement portion formed on the proximal portion of the knife includes an annular convex portion that is received within the annular recess defined by the plurality of resilient fingers of the knife carrier to releasably secure the knife to the knife carrier, the resilient fingers flexing outwardly upon application of the predetermined force to the knife to facilitate release of the knife from the knife carrier, and wherein the second engagement portion is formed on the proximal portion of the knife by inverting the proximal portion of the knife.

2. The stapling device of claim 1, wherein the anvil assembly includes an anvil head and a center rod, the anvil head pivotably coupled to the center rod and movable from an operative position to a tilted position.

3. A knife assembly comprising:
a knife carrier having a distal portion defining a first engagement portion defined by a plurality of resilient fingers formed on the distal portion of the knife carrier, each of the plurality of resilient fingers having a concave surface to define an annular recess about the distal portion of the knife carrier; and
an annular knife having a proximal portion and a distal portion, the distal portion defining a cutting edge, the proximal portion defining a second engagement portion that is coupled to the first engagement portion to releasably secure the knife to the knife carrier, one of the first or second engagement portions formed of a resilient material that is deformable to allow the first engagement portion to separate from the first engagement portion, wherein the knife can be uncoupled from the first engagement portion of the knife carrier upon application of a predetermined force to the knife,
wherein the second engagement portion formed on the proximal portion of the knife includes an annular convex portion that is received within the annular recess defined by the plurality of resilient fingers of the knife carrier to releasably secure the knife to the knife carrier, the resilient fingers deforming outwardly upon application of the predetermined force to the knife to facilitate release of the knife from the knife carrier, and wherein the second engagement portion is formed on the proximal portion of the knife by inverting the proximal portion of the knife.

* * * * *